United States Patent [19]

Chiffon et al.

[11] Patent Number: 5,195,048
[45] Date of Patent: Mar. 16, 1993

[54] SYSTEM AND METHOD FOR EXHAUSTING VAPOR FROM A HEATED PRESSURE CHAMBER

[75] Inventors: Mark E. Chiffon, Erie; Thomas G. Cook, Fairview; Conrad J. Geibel, Erie, all of Pa.

[73] Assignee: American Sterilizer Company, Erie, Pa.

[21] Appl. No.: 662,138

[22] Filed: Feb. 26, 1991

[51] Int. Cl.⁵ .............................................. A61L 2/06
[52] U.S. Cl. ........................... 364/551.01; 364/558; 422/110; 137/12
[58] Field of Search ............... 364/551.01, 550, 558, 364/509, 571.02, 571.05, 166; 137/2, 12; 422/26, 110, 112, 113

[56] References Cited

U.S. PATENT DOCUMENTS

| | | | |
|---|---|---|---|
| 4,241,010 | 12/1980 | Baran | 422/112 |
| 4,759,909 | 7/1988 | Joslyn | 422/110 |
| 4,781,898 | 11/1988 | Jones | 422/112 |
| 4,971,764 | 11/1990 | Albright | 422/110 |

Primary Examiner—Thomas G. Black
Assistant Examiner—Michael Zanelli
Attorney, Agent, or Firm—Kirkpatrick & Lockhart

[57] ABSTRACT

A system and method of exhausting vapor, such as steam, from a pressure chamber following the sterilization phase of a sterilization cycle under superatmospheric pressure conditions are provided. The system and method preferably employ a microprocessor and an appropriate pressure transducer to measure the chamber pressure at the conclusion of the vapor exposure period to determine an initial chamber pressure. The method includes the further steps of exhausting vapor from the chamber for a period of time, preferably up to about one minute, to lower the chamber pressure, measuring the chamber pressure at the conclusion of such first period of time to determine a second chamber pressure and calculating the difference between the initial chamber pressure and the second chamber pressure to determine an exhaust rate. The exhaust rate is used to predetermine successively lower next target chamber pressures to be reached at the conclusion of successive intervals of a predetermined second period of time, such as three seconds, until a predetermined final chamber pressure is reached. Vapor is exhausted from the chamber during each successive interval of the second period of time until the target chamber pressure for that particular second period of time is reached. After each such interval of time, the chamber pressure is measured to determine whether the calculated next target chamber pressure has been reached.

10 Claims, 7 Drawing Sheets

SYSTEM AND METHOD FOR EXHAUSTING VAPOR FROM A HEATED PRESSURE CHAMBER

BACKGROUND OF THE INVENTION

1. Field of the Invention

The present invention relates to systems and methods for exhausting enclosed chambers and, more particularly, to a system and method for exhausting vapor from a heated pressure chamber.

2. Description of the Invention Background

Sterile solutions or fluids are useful for a variety of purposes in clinical practice. For example, solutions may be administered to a patient parenterally, given orally, applied to the skin or used to irrigate or bathe body tissues, organs and wounds. Such solutions must be sterilized prior to use. They are often sterilized in capped containers in which the solution can be stored for long periods while maintaining sterility.

Moist heat in the form of saturated steam under pressure is one of the most dependable agents for the destruction of all forms of microbial life. Steam sterilization is frequently used to sterilize liquids in containers. A problem incident to the steam sterilization of liquid loads is liquid loss due to boiling of the liquid during the exhaust phase of the sterilization cycle if the exhaust is too fast. Another problem is the extended cycle time caused by the current method of exhausting and cooling sterilization chambers.

Saturated steam is water vapor in the condition in which it is generated from water. During the heating process, steam formed near the surface of the heating element rises to the surface of the water and breaks through. The steam released into the space above the liquid is saturated steam. The steam-free water is known as saturated water and is at the same temperature as the saturated steam. The temperature is known as the saturation temperature. Saturated steam undergoes a reduction in temperature when it undergoes a reduction in pressure and vice versa. The relationship between temperature and pressure for saturated steam follows a curve shown in FIG. 1. The phase-boundary curve for saturated steam is also representative of the vapor pressure of water.

During the sterilization phase of a steam sterilization cycle, there is no liquid loss in the containers of liquid because the steam pressure in the chamber is equal to or above that which is necessary to induce boiling of the liquid in the containers. When the pressure is reduced in the exhaust phase following the sterilization phase, boiling of the liquid in the containers may occur if the pressure in the chamber is reduced faster than the temperature drop so that the pressure reaches a point lower than the pressure necessary to maintain the temperature of the liquid at its saturated steam point. If the exhaust rate is too rapid, violent boiling may occur, resulting in the explosion of the containers. The precise relationship between the liquid in the containers and the pressure in the chamber depends on the kind of liquid.

To avoid such dire consequences, some sterilization cycles employ exhaust rates based on the worst case load conditions. The worst case load assumption results in increased cycle times which in turn results in a considerable reduction in sterilizer efficiency. Exhaustion is generally non-linear and through a single fixed orifice. An alternative method heretofore used to avoid boiling of the liquid in the containers provides an exhaust rate which is adjustable by the operator to account for variations in load types and sizes. The adjustable exhaust rates which can be set in some commercially available sterilizers are linear. The operator adjusted exhaust rates increase the efficiency of the sterilization cycle but also increase the potential for human error. If the operator sets the exhaust rate too fast, boiling may occur and the containers may explode. To avoid the possibility of error, some operators set the exhaust rate lower than necessary, thereby decreasing efficiency and nullifying the advantage to an operator adjustable exhaust rate.

Thus, there is a need for a method for determining the optimal rate for exhausting vapor, such as steam, from a pressure chamber in a safe, efficient manner. There is a further need for such a method which is not subject to human error. Finally, there is a need for a method for determining the optimal rate for exhausting vapor from a pressure chamber which can be run automatically.

SUMMARY OF THE INVENTION

The present invention provides a system and method for exhausting vapor, such as steam, from a heated pressure chamber following a period during which a load of items in the chamber is exposed to the vapor under superatmospheric pressure conditions. The method includes the steps of measuring the chamber pressure at the conclusion of the vapor exposure period to determine an initial chamber pressure, exhausting vapor from the chamber for a first period of time to lower the chamber pressure, then measuring chamber pressure at the conclusion of the first period of time to determine a second chamber pressure. The difference between the initial chamber pressure and the second chamber pressure is calculated to determine an exhaust rate.

The exhaust rate is then used to calculate a target chamber pressure for the conclusion of one interval of a predetermined second period of time. Vapor is then exhausted from the chamber for one interval of such second period of time to lower the chamber pressure to the target chamber pressure. If the target chamber pressure is reached during the interval of such second period of time, the exhaustion of vapor is discontinued for the remainder of that time period. At the conclusion of that interval, the chamber pressure is measured to determine whether the target chamber pressure has been reached. If the target chamber pressure has not been reached, the exhaust rate is used with the measured chamber pressure to calculate a further target chamber pressure. If, however, the target chamber pressure has been reached, the exhaust rate is used with the target chamber pressure to calculate a further target chamber pressure. The steps of (i) exhausting vapor from the chamber for one interval of the second period of time; (ii) measuring the chamber pressure during such interval of the second period of time to determine whether the target chamber pressure has been reached, and, if reached, discontinuing the exhaustion of vapor for the remainder of that time period; and (iii) calculating a further target chamber pressure; are repeated to reach progressively lower chamber pressures over successive intervals of the second period of time until a predetermined final chamber pressure is reached.

The pressure chamber of the system and method of the present invention preferably includes two valves, a first valve and a second valve. The second valve has an opening which is larger than the opening of the first valve. Vapor is initially exhausted through the first valve for both of the two exhaustion steps of the method. When the measured chamber pressure at the conclusion of an interval of the second period of time is greater than the target chamber pressure for five successive intervals of the second time period, the step of further exhausting vapor from the chamber is conducted by exhausting the vapor through the second, larger valve. All further steps of exhausting vapor from the chamber are conducted by exhausting the vapor from the second valve.

The method may further include the step of decreasing the calculated exhaust rate by a predetermined amount and using such decreased exhaust rate for the calculations used to predetermine each target chamber pressure during the remainder of the method. The decrease in the exhaust rate is intended to account for variations in load character.

In a preferred embodiment of the invention, the vapor is steam which is generated during a steam sterilization process and the goods to be sterilized are containers of water or aqueous solutions. The first period of time is preferably a time, up to about one minute, which is sufficient to establish an exhaust curve which generally follows the saturated steam/pressure curve suitable for the type and size of load in the chamber.

The system and method of the invention are preferably automatically carried out by the use of a microprocessor programmed to receive the chamber pressure measurements, to store such measurements, to calculate the exhaust rate and to calculate each target chamber pressure level over a predetermined period of time. Each interval of the second period of time may be, for example, three seconds. A microprocessor can be programmed to repeat certain of the steps, e.g., exhausting vapor from the chamber for the three second interval, measuring the chamber pressure during such three second interval and calculating the next target chamber pressure.

The present invention fulfills the need which exists for a method for exhausting vapor, such as steam, from a pressure chamber in a safe, efficient manner. The present invention further fulfills the need for such a method which is not subject to human error and which can be run automatically. These and other advantages and benefits of the present invention will become apparent from the description of a preferred embodiment hereinbelow.

BRIEF DESCRIPTION OF THE DRAWINGS

The present invention can be better understood by reference to the drawings in which.

DETAILED DESCRIPTION OF THE PREFERRED EMBODIMENTS

Figure 2:
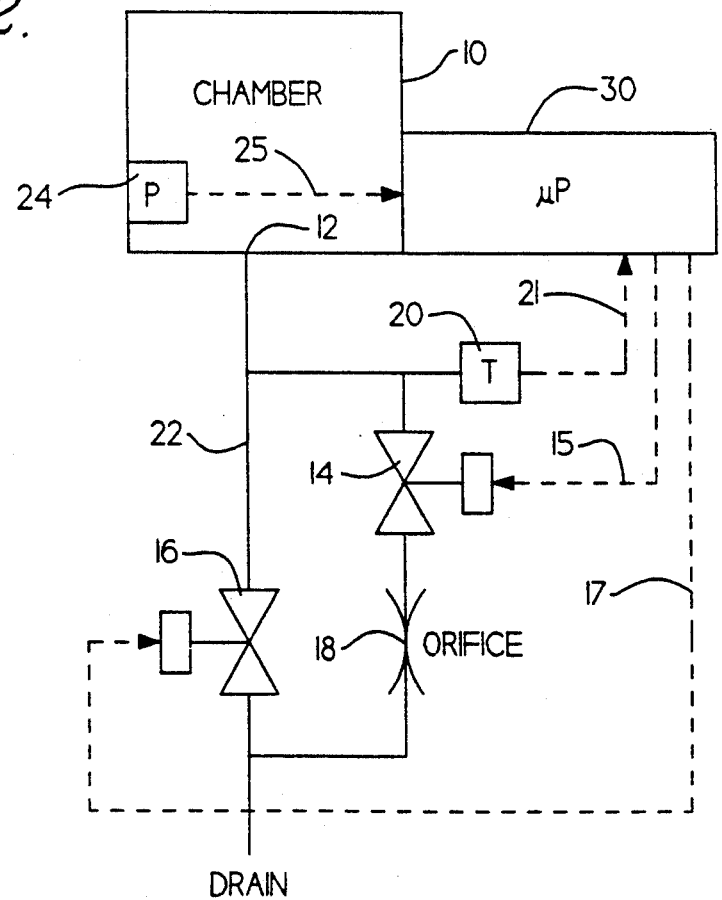
FIG. 2 is a diagram of a pressure chamber in which the system and method of the present invention may be practiced.

FIG. 2 illustrates a pressure chamber 10 in which selected items are processed and, pursuant to such processing, are exposed, for a period of time, to a vapor under superatmospheric pressure conditions. For purposes of the detailed description of the invention, the chamber 10 will be described as a sterilization chamber, the process as a sterilization process and the vapor as steam. The system and method of the present invention are particularly well suited for use when the selected items to be processed are capped containers of an aqueous solution, such as parenteral solutions, water for use in irrigating deep wounds or bathing tissues and organs and topical solutions.

Referring to FIG. 2, the chamber 10 has a drain opening 12 leading to a drain line 22 in which two exhaust valves, a slow exhaust valve 14 and a fast exhaust valve 16, are positioned to control the flow rate of vapor exhausted from the chamber 10. The opening of slow exhaust valve 14 is smaller in diameter than the opening of fast exhaust valve 16 and opens to an orifice 18 which is smaller in diameter than the opening into which fast exhaust valve 16 leads. A temperature probe 20 is positioned in the drain line 22 adjacent to the drain opening 12. A pressure transducer 24 is in communication with chamber 10 to sense the chamber pressure.

A microprocessor 30 is preferably provided to receive data from the temperature probe 20 and the pressure transducer 24, through communications lines 21 and 25, respectively, to store certain of the data in an internal memory (not shown), perform calculations based on such data and control the opening and closing of valves 14 and 16, through control lines 15 and 17, respectively, in response to the data received and the calculations made.

Figure 1:
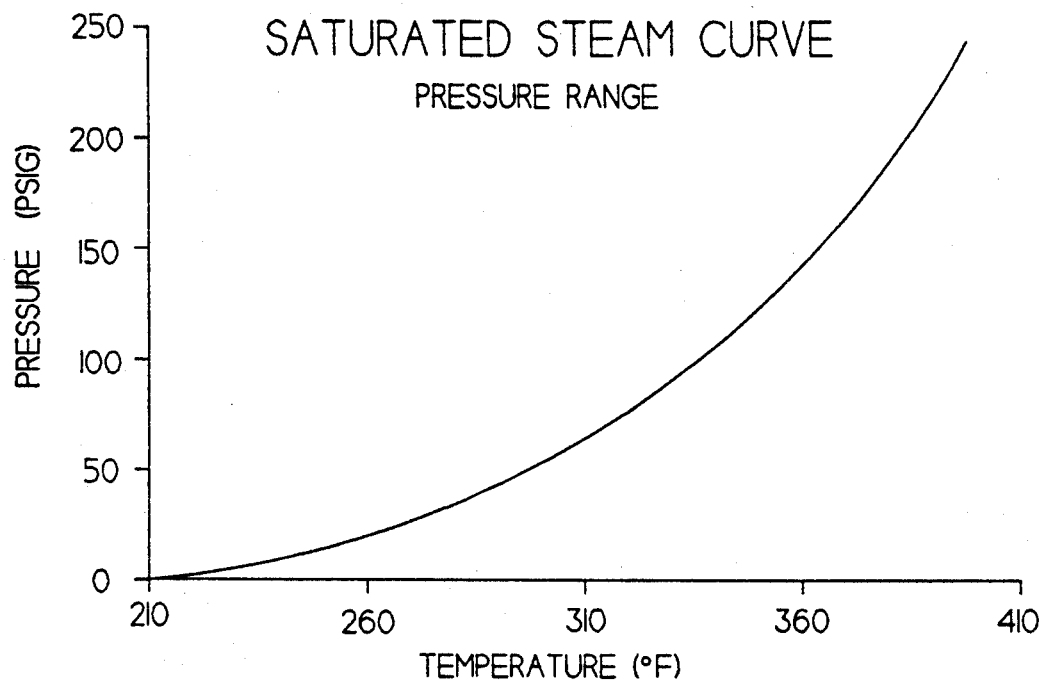
FIG. 1 is a graph of the relationship between pressure and temperature in saturated steam.

In the preferred embodiment of the system and method of the present invention, steam is exhausted from chamber 10 in a controlled manner to progressively lower the chamber pressure to a desired final pressure level and to permit the liquid in the containers to gradually cool at a rate comparable to the saturated steam/pressure curve shown in FIG. 1 to avoid boiling and thereby losing liquid due to either its evaporation or the explosion of the containers. The control system offered by the microprocessor 30 automatically determines the optimal exhaust rate for each particular type and size of load being processed. The optimal load exhaust rate is selected automatically, thus providing for the safe and efficient processing of a variety of loads.

The size of the orifice 18 through which steam is exhausted varies with chamber size and is determinative of the exhaust rate through the slow exhaust valve 14. The system and method of the present invention calculate an optimum exhaust rate based on the particular conditions within the chamber 10, including not only load type and size, but the chamber size and the size of the exhaust valves 14 and 16 as well.

Figure 3:
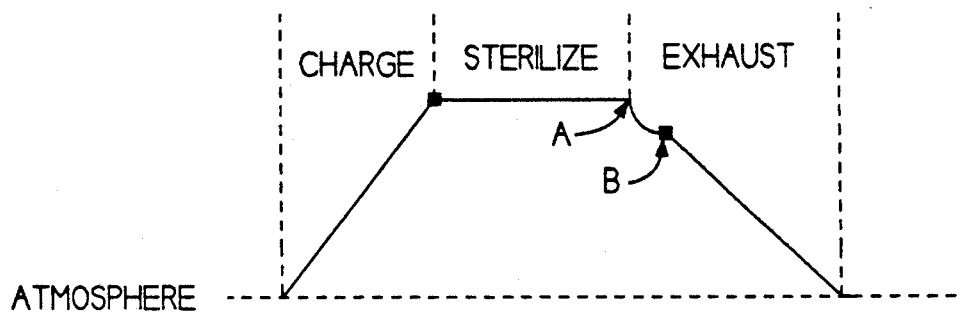
FIG. 3 is a graph of a sterilization cycle showing the exhaust rate for a first period of time.
Figure 4:
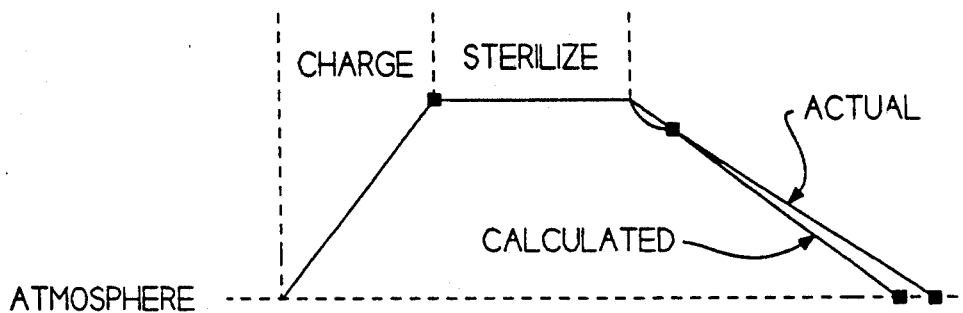
FIG. 4 is a graph of a sterilization cycle showing the actual exhaust rate compared to a calculated exhaust rate for the remainder of the exhaust phase of the cycle.

During a typical sterilization process there is a conditioning and charge phase, a sterilization phase and an exhaust and cooling phase. Referring to the graphs of FIGS. 3 through 5, it can be seen that during the charge phase the chamber pressure is gradually increased above atmospheric pressure. During the sterilization phase, the chamber pressure remains at superatmospheric levels for a period of time sufficient to sterilize the items within the chamber 10. Upon completion of the sterilization phase, the exhaust phase begins wherein the chamber 10 is gradually exhausted.

Figure 6A:
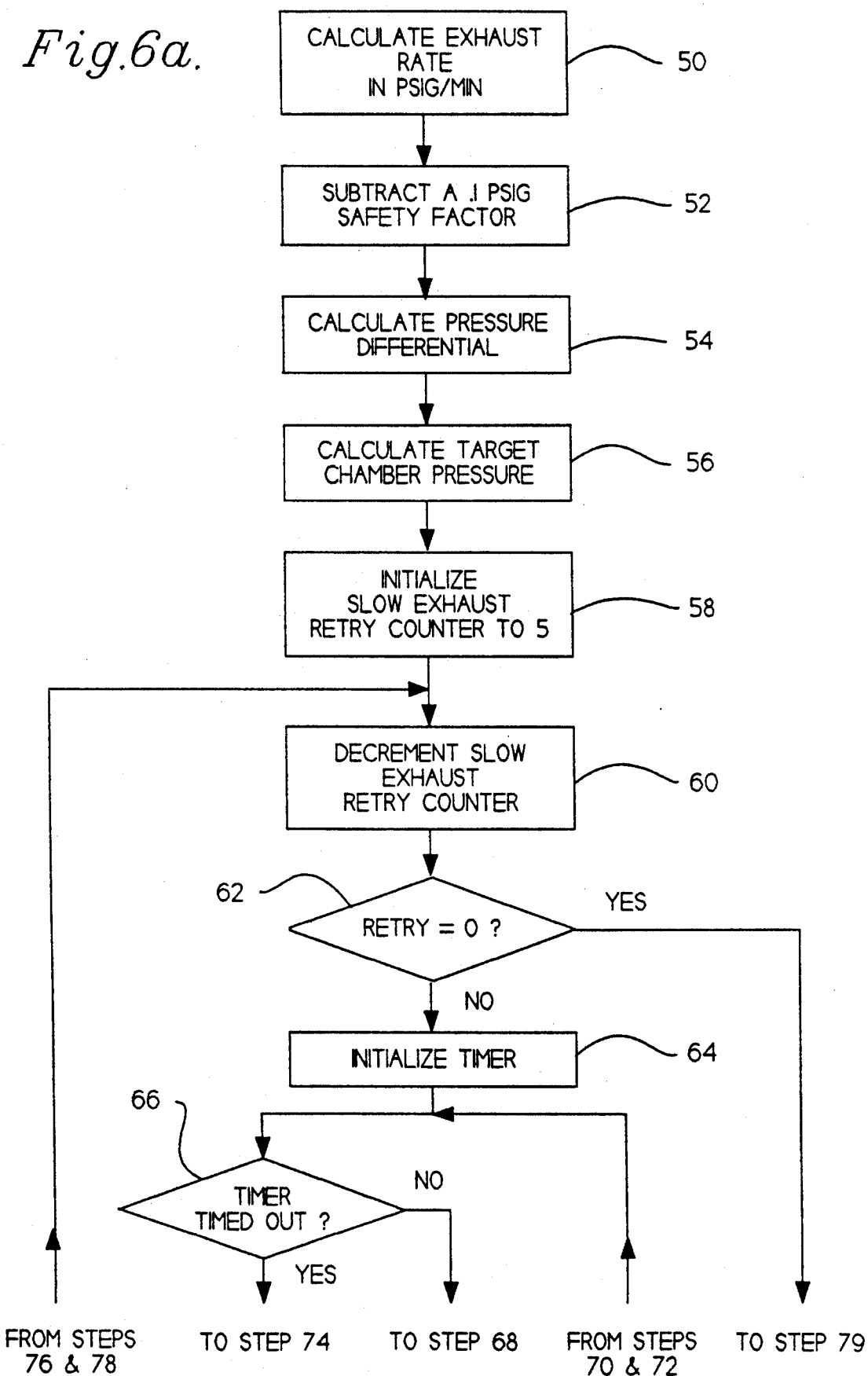
FIGS. 6a through 6c depict a flow chart showing a preferred series of steps performed by a microprocessor in automatically carrying out the system and method of the present invention.

The system and method of the present invention relate to the exhaust phase of the sterilization process and will be described through the use of the flow charts depicted in FIGS. 6a through 6c. In step 50 of the flow chart of FIG. 6a, an exhaust rate of the chamber 10 is calculated. A first chamber pressure is measured by means of pressure transducer 24 at a time corresponding to the point labeled "A" in the graph of FIG. 3. The point labeled "A" corresponds to both the conclusion of the sterilization phase wherein the containers of liquid are exposed to steam and the beginning of the exhaust phase. The first chamber pressure measurement is communicated to the microprocessor 30 through communications line 25 and stored in the internal memory (not shown) of microprocessor 30.

The exhaust phase of the sterilization process then begins. Steam is exhausted from chamber 10 through slow exhaust valve 14 and orifice 18. At the end of a first period of time, represented in FIG. 3 by the letter "B", preferably a period of time up to about one minute, and more preferably a period between and about thirty seconds and about one minute, a second chamber pressure is measured by means of pressure transducer 24. The escape of steam from the chamber 10 initially occurs very quickly. Thus, time periods much less than thirty seconds will provide a less accurate representation of the actual exhaust rate. The second chamber pressure measurement is communicated to the microprocessor 30 through communications line 25 and stored in the internal memory (not shown) of microprocessor 30. The microprocessor 30 then calculates a difference between the second chamber pressure measurement and the first chamber pressure measurement and applies an appropriate scaling factor to the difference, the scaling factor depending on the time interval between the two pressure measurements, to arrive at a calculated exhaust rate in psig/min.

Program control continues with step 52 where a safety factor may be introduced to the calculated exhaust rate by decrementing the exhaust rate by 0.1 psig/min. This optional safety factor is designed to accommodate variations in load type and cap configuration. Program control then continues with step 54 where, in the preferred embodiment of the invention, a three second pressure differential is calculated by dividing the calculated exhaust rate in psig/min. by 20. The pressure differential time period need not be three seconds. The pressure differential time period should, however, be consistent throughout the exhaust phase of the sterilization process to ensure a gradual decrease in chamber pressure. Thus, any suitable pressure differential time period may be chosen.

Program control continues with step 56 where the microprocessor 30 calculates a target chamber pressure. The target chamber pressure is derived by subtracting the pressure differential calculated in step 54 from the second chamber pressure measurement taken in step 50 (corresponding to point "B" in the graph of FIG. 3). In step 58, a slow exhaust retry counter is initialized. This counter may be initialized, for example, to a value of five. The initialization value for the slow exhaust retry counter is variable and will depend on the actual exhaust characteristics of the sterilization chamber 10.

Program control then continues with step 60 where the slow exhaust retry counter is decremented by one.

In step 62, the microprocessor 30 determines whether the slow exhaust retry counter is equal to zero. If the slow exhaust retry counter is equal to zero, program control is transferred to step 79; otherwise, program control continues with step 64 where a software timer is initialized to the pressure differential time period utilized in step 54. The timer may be initialized in the preferred embodiment of the invention, for example, to three seconds.

Program control continues with step 66 where the microprocessor 30 determines whether the timer has timed out. If the timer has timed out, program control continues with step 74; otherwise, program control continues with step 68 shown in FIG. 6b where the microprocessor 30 reads the chamber pressure as measured by the pressure transducer 24. The chamber pressure is transmitted to the microprocessor 30 through communications line 25. The chamber pressure is then compared to the target chamber pressure calculated in step 56. If the actual chamber pressure is not greater than the target chamber pressure, the microprocessor 30, in step 70, sends a signal, via control line 15, to close slow exhaust valve 14. The slow exhaust retry counter is also reset, in step 70, to the initialization value as used in step 58. If the microprocessor 30 determines, in step 68, that the actual chamber pressure is greater than the target chamber pressure, the microprocessor 30, in step 72, sends a signal via control line 15 to open slow exhaust valve 14. Following either step 70 or step 72, program control returns to step 66.

The result is that slow exhaust valve 14 is opened to exhaust vapor from chamber 10 for an interval of time equal to three seconds so as to attempt to reduce the actual chamber pressure to a level corresponding to the target chamber pressure. However, if the actual chamber pressure reaches the target chamber pressure before the end of the three second interval, the slow exhaust valve 14 is closed for the remainder of that time interval.

Figure 6B:
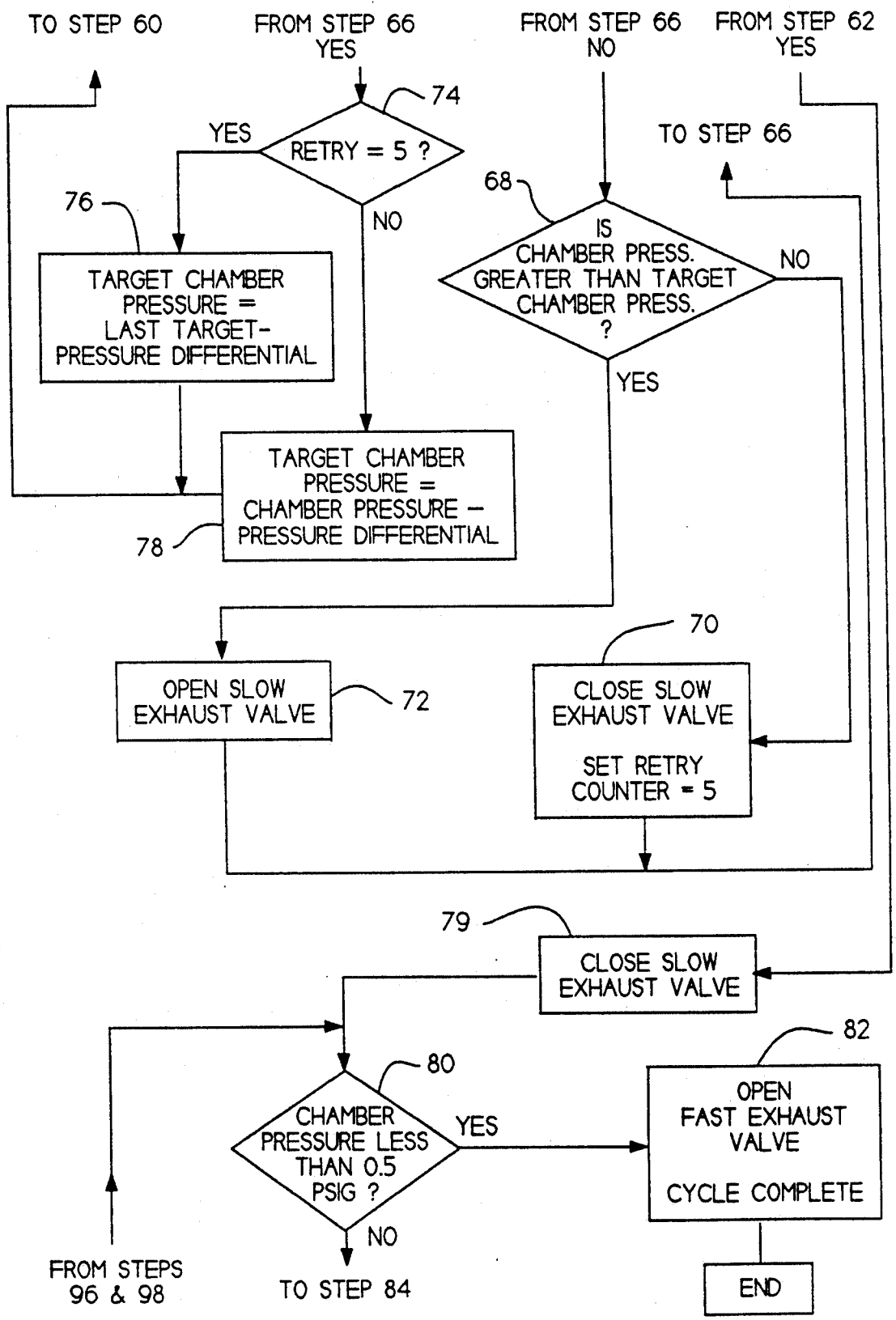
Figure 6C:
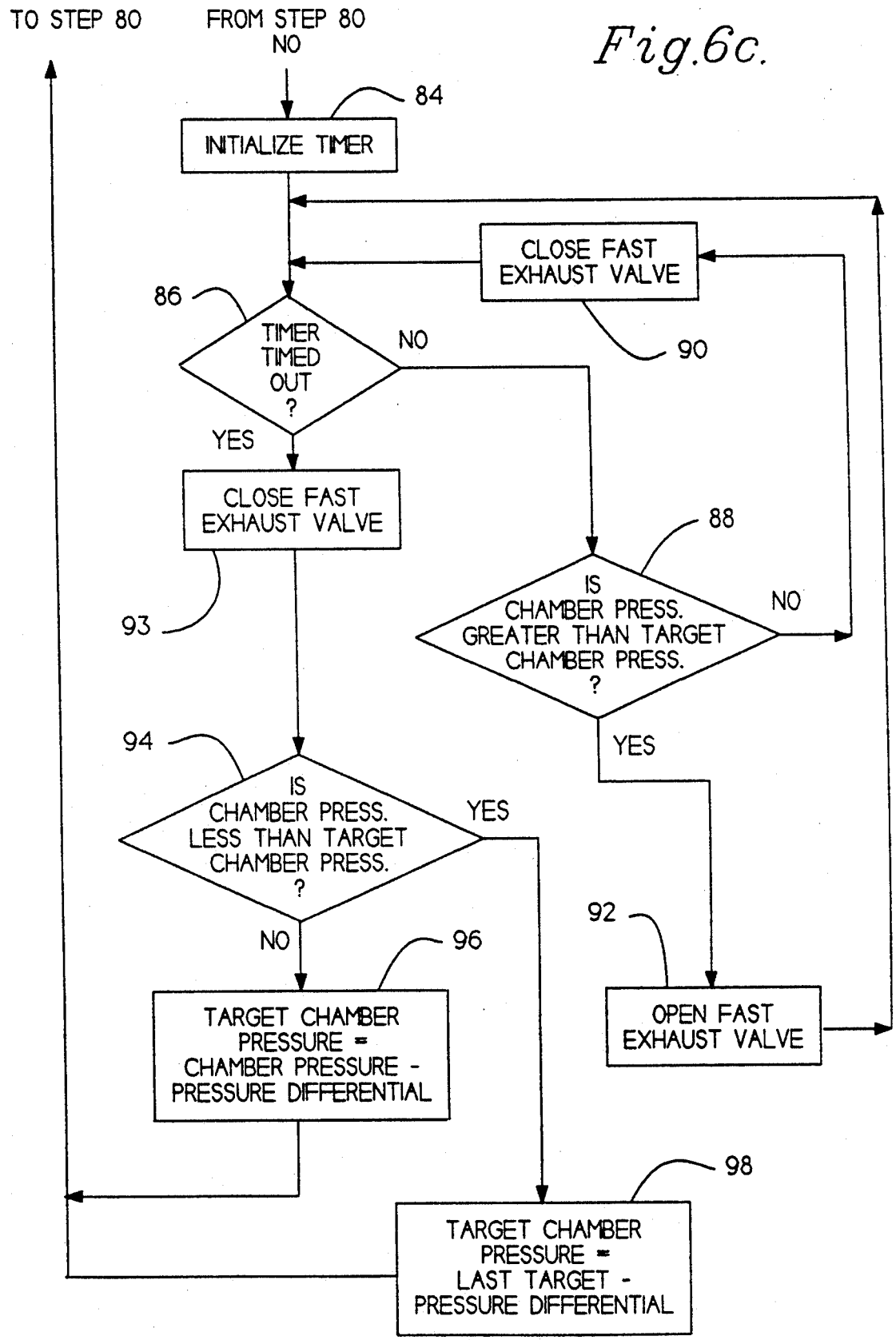

If the microprocessor 30 determines in step 66 that the timer has timed out, program control continues with step 74 shown in FIG. 6b where the microprocessor 30 determines whether the slow exhaust retry counter is equal to five thus indicating that the target chamber pressure has been reached. If the target chamber pressure has not been reached, the microprocessor 30, in step 78, calculates a new target chamber pressure by subtracting the pressure differential calculated in step 54 from the chamber pressure read by the microprocessor 30 in step 68. Program control then returns to step 60. If the target chamber pressure has been reached, the microprocessor 30, in step 76, calculates a new target chamber pressure by subtracting the pressure differential calculated in step 54 from the previous target chamber pressure. Program control then returns to step 60.

If the target chamber pressure is not reached for five successive pressure measurements, as is determined in step 62, the microprocessor 30 transfers program control to step 79 shown in FIG. 6b where the microprocessor 30 transmits a control signal over control line 15 to close slow exhaust valve 14. The larger fast exhaust valve 16 will be opened to exhaust steam from chamber 10 during each subsequent three second interval of the exhaust phase. After slow exhaust valve 14 is opened during the first few pressure differential time periods, the chamber pressure drops so that there is insufficient force to exhaust steam through the slow exhaust valve 14. As a result, the larger, fast exhaust valve 16 is then opened while the slow exhaust valve 14 is closed.

In step 80, microprocessor 30 reads the chamber pressure as measured by the pressure transducer 24 and communicated to the microprocessor 30 via communications line 25. The microprocessor 30 then determines whether the chamber pressure is less than 0.5 psig. If the chamber pressure is less than 0.5 psig, program control continues with step 82 where the microprocessor 30 transmits a control signal over control line 17 to open fast exhaust valve 16 to complete the sterilization process. If the chamber pressure is greater than 0.5 psig, program control continues with step 84 shown in FIG. 6c where a software timer is initialized to the same pressure differential time period utilized in step 54. Program control then continues with step 86 where the microprocessor 30 determines whether the timer has timed out. If the timer has timed out, program control continues with step 93; otherwise, program control continues with step 88 where the microprocessor 30 reads the chamber pressure as measured by the pressure transducer 24. The chamber pressure is transmitted to the microprocessor 30 through communications line 25. The chamber pressure is then compared to the target chamber pressure. If the actual chamber pressure is not greater than the target chamber pressure, the microprocessor 30, in step 90, sends a signal via control line 17 to close fast exhaust valve 16. If the actual chamber pressure is greater than the target chamber pressure, the microprocessor 30, in step 92, sends a signal via control line 17 to open fast exhaust valve 16. Following either step 90 or step 92, program control returns to step 86.

If the microprocessor 30 determines, in step 86, that the timer has timed out, program control continues with step 93 where the microprocessor 30 sends a signal via control line 17 to close fast exhaust valve 16. Program control then continues with step 94 where the microprocessor 30 determines whether the actual chamber pressure as measured in step 88 is less than the target chamber pressure. If the target chamber pressure has not been reached, the microprocessor 30, in step 96, calculates a new target chamber pressure by subtracting the pressure differential calculated in step 54 from the chamber pressure read by the microprocessor 30 in step 88. Program control then returns to step 80. If the target chamber pressure has been reached, the microprocessor 30, in step 98, calculates a new target chamber pressure by subtracting the pressure differential from the previous target chamber pressure. Program control then returns to step 80.

Thus, at the end of each three second time interval, the chamber pressure is measured and the next target chamber pressure is calculated. It is expected that, in most applications, during the first few pressure differential time periods in which the fast exhaust valve 16 is used to exhaust steam, the valve 16 will be open for only a portion of each three second time interval. After the pressure differential drops further, however, the valve 16 will remain open for most or substantially all of each subsequent three second time period.

Figure 5:
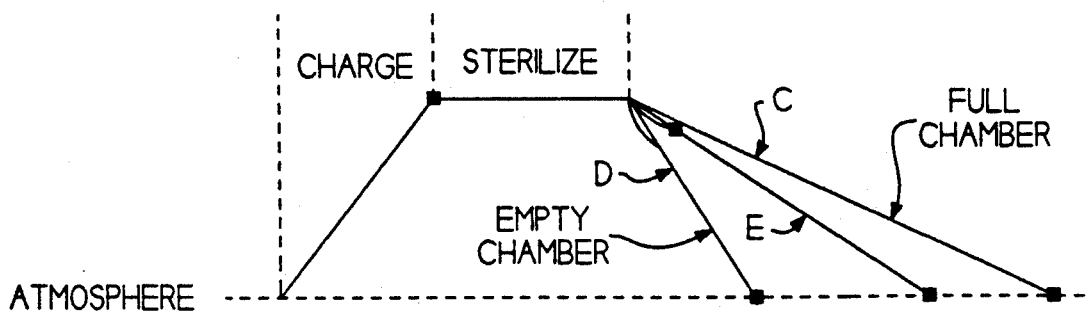
FIG. 5 is a graph of a sterilization cycle comparing the exhaust rates of three different load conditions.

The exhaust rate will be different for different loads. FIG. 5 illustrates three different exhaust curves. Large loads are presented by line "C". The exhaust rate experienced in an empty chamber is shown by line "D" of FIG. 5 and the exhaust rate of a chamber only partially loaded is shown by line "E" of FIG. 5. Larger loads, as shown, experience a slower exhaust rate than smaller loads.

Exhaust times in a 36×24×48 cubic inch chamber have been found to be reduced for a full load of 154 one-thousand milliliter bottles by 400% and for a minimum load of one one-thousand milliliter bottle by 50%.

EXAMPLE 1

Figure 7:
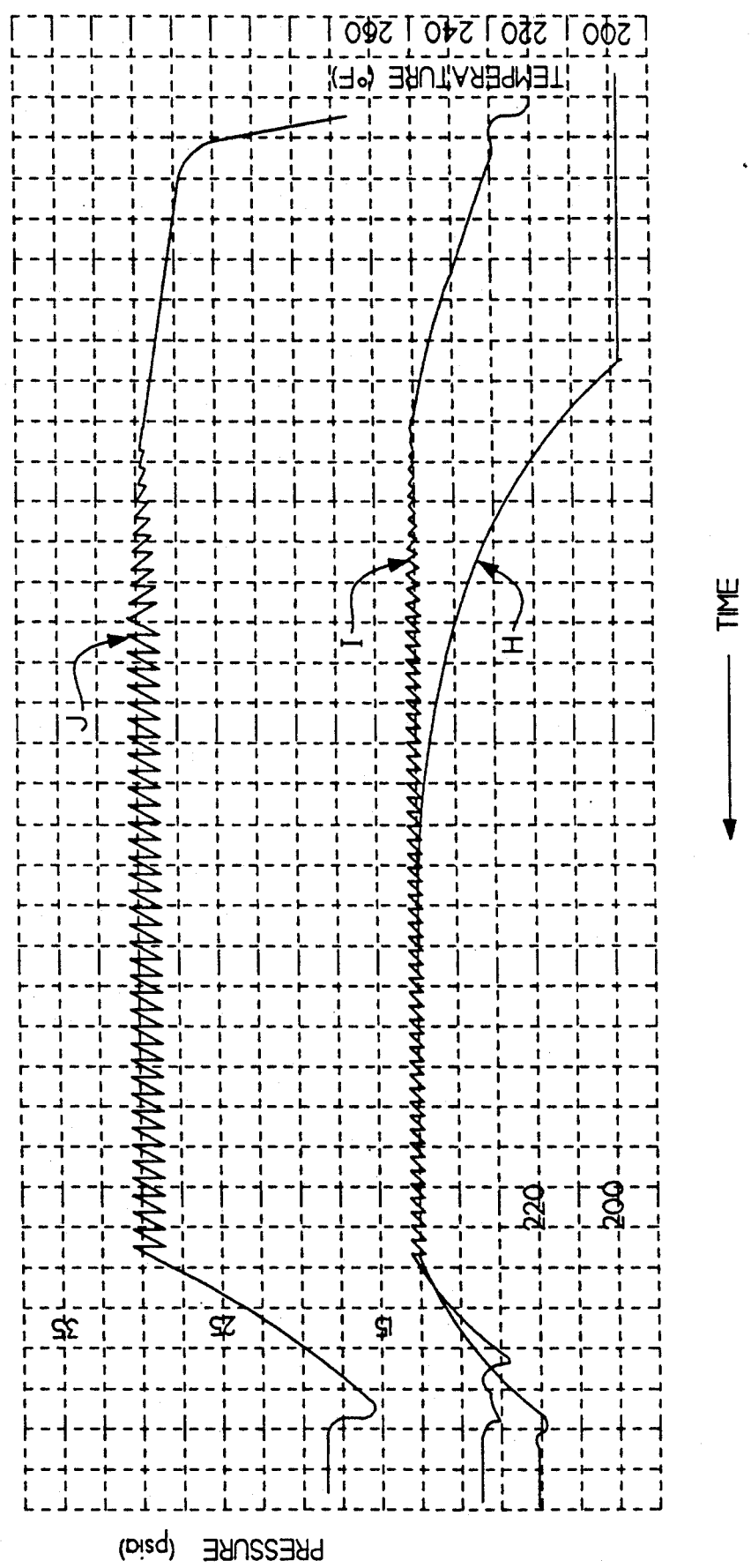
FIGS. 7 and 8 are cycle graphs representative of sterilization cycles in which the system and method of the present invention were used to exhaust the chamber.

In a sterilization cycle run at 250° F., 154 flasks holding 1,050 ml of water were sterilized. The duration of the sterilization phase of the cycle was 45 minutes. The calculated exhaust rate after one minute of exhaust time was 2.12 psi/min. The actual rate was 1.8 psi/min. A cycle graph representative of that sterilization cycle is shown in FIG. 7. A temperature probe was placed in the center flask as indicative of the worst case temperature in the load. The graph of FIG. 7 illustrates the temperature curve for the center flask as line H, the temperature curve for the chamber, as measured by temperature probe 20, as line I and a pressure curve as line J. The initial and final weights of five flasks were determined to calculate the percentage of water lost. The results are shown in Table 1 below.

TABLE 1

| Flask | Initial wt. (g) | Final wt. (g) | % Loss |
|---|---|---|---|
| 1 | 1831.3 | 1793.7 | 2.05 |
| 2 | 1833.6 | 1795.3 | 2.31 |
| 3 | 1821.9 | 1772.4 | 2.7 |
| 4 | 1838.9 | 1804.1 | 1.89 |
| 5 | 1838.1 | 1807.8 | 1.65 |

EXAMPLE 2

Figure 8:
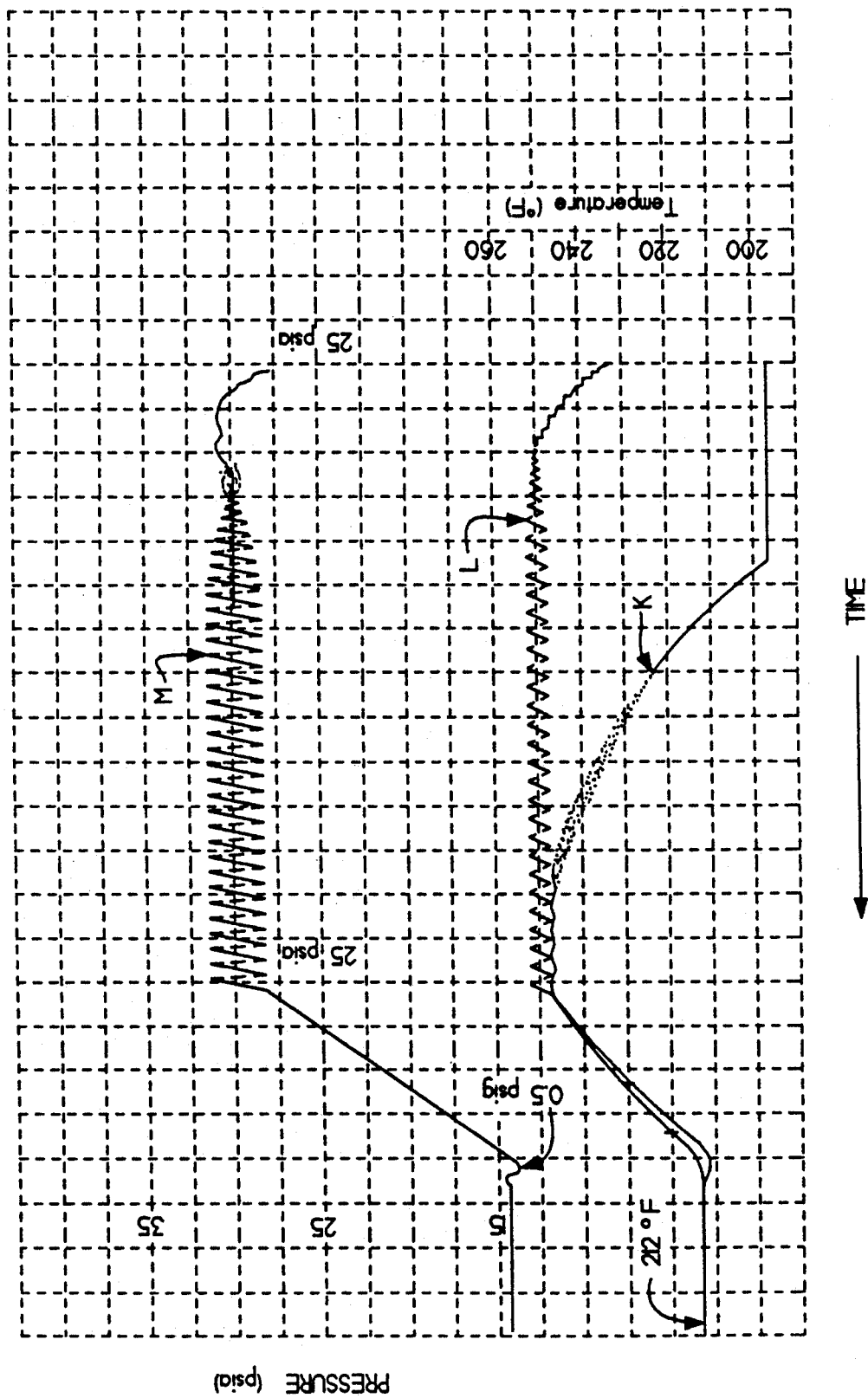

The cycle graph shown in FIG. 8 is representative of a sterilization cycle run on a 7 gallon load. The temperature of the load, represented by the center flask, and the temperature of the chamber are shown by lines K and L, respectively. The chamber pressure is represented by line M. The chamber pressure at the end of the exhaust phase was 0.5 psig. The pressure during the sterilization phase was between about 29 and 31 psia. The pressure measured after one minute of exhaust was 25 psia. The exhaust rate calculated was 2.23 psi/min.

While the present invention has been described in connection with an exemplary embodiment thereof, it will be understood that many modifications and variations will be readily apparent to those of ordinary skill in the art. This disclosure and the following claims are intended to cover all such modifications and variations.

What we claim is:

1. A method for exhausting vapor from a pressure chamber for processing loads following a vapor exposure period under superatmospheric pressure conditions, said method comprising the steps of:
   (a) measuring chamber pressure at the conclusion of the exposure period to determine an initial chamber pressure;
   (b) exhausting vapor from the chamber for a predetermined first period of time to lower the chamber pressure;
   (c) measuring chamber pressure at the conclusion of said first period of time to determine a second chamber pressure;
   (d) calculating a difference between said initial chamber pressure and said second chamber pressure to determine an optimal pressure differential;

(e) calculating a difference between said second chamber pressure and said optimal pressure differential to predetermine a target chamber pressure to be reached at the conclusion of one interval of a predetermined second period of time;

(f) exhausting vapor from the chamber for said one interval of said second period of time to lower the chamber pressure to said target chamber pressure predetermined in the immediately preceding calculating step;

(g) measuring the chamber pressure during said one interval of said second period of time to determine whether said target chamber pressure has been reached;

(h) discontinuing the exhaustion of vapor from the chamber when said target chamber pressure has been reached;

(i) if said target chamber pressure has not been reached by the conclusion of said one interval of said second period of time, calculating a difference between the chamber pressure measured in step (g) and said pressure differential to predetermine a further target chamber pressure to be reached at the conclusion of an additional interval of said second period of time and repeating steps (f) through (i) to reach progressively lower chamber pressures over successive intervals of said second period of time until a predetermined final chamber pressure is reached; or (j) if said target chamber pressure has been reached by the conclusion of said one interval of said second period of time, calculating a difference between said target chamber pressure predetermined in step (e) and said pressure differential to predetermine a further target chamber pressure to be reached at the conclusion of an additional interval of said second period of time and repeating steps (f) through (j) to reach progressively lower chamber pressures over successive intervals of said second period of time until a predetermined final chamber pressure is reached.

2. The method recited in claim 1 wherein vapor is exhausted from the chamber in step (b) and in step (f) through a first exhaust valve until said target chamber pressure cannot be reached following exhaustion of vapor for a predetermined number of successive intervals of said second period of time, whereupon vapor is thereafter exhausted from the chamber through a second exhaust valve, said second exhaust valve being larger than said first exhaust valve.

3. The method recited in claim 2 wherein said predetermined number of successive intervals is equal to five.

4. The method recited in claim 1 further comprising the step of decreasing said optimal pressure differential by a predetermined amount and using such decreased optimal pressure differential for calculating said target chamber pressure during the remainder of the method.

5. The method recited in claim 1 wherein said vapor is steam, said load is at least one container of an aqueous solution and said first period of time is a time, up to about one minute, sufficient to establish an exhaust curve which follows a saturated steam/pressure curve suitable for the type and size of load in the chamber.

6. A system for exhausting vapor from a pressure chamber for processing loads following a vapor exposure period under superatmospheric pressure conditions, comprising:

(a) first means for measuring chamber pressure at the conclusion of the exposure period to determine an initial chamber pressure;

(b) second means for exhausting vapor from the chamber for a predetermined first period of time to lower the chamber pressure;

(c) third means for measuring chamber pressure at the conclusion of said first period of time to determine a second chamber pressure;

(d) fourth means for calculating a difference between said initial chamber pressure and said second chamber pressure to determine an optimal pressure differential;

(e) fifth means for calculating a difference between said second chamber pressure and said optimal pressure differential to predetermine a target chamber pressure to be reached at the conclusion of one interval of a predetermined second period of time;

(f) sixth means for exhausting vapor from the chamber for said one interval of said second period of time to lower the chamber pressure to said target chamber pressure;

(g) seventh means for measuring chamber pressure during said one interval of said second period of time to determine whether said target chamber pressure has been reached;

(h) eighth means for discontinuing the exhaustion of vapor from the chamber when said target chamber pressure has been reached;

(i) ninth means for calculating a difference between the chamber pressure measured during said one interval of said second period of time and said optimal pressure differential, if said target chamber pressure has not been reached by the conclusion of said one interval of said second period of time, to predetermine a further target chamber pressure to be reached at the conclusion of an additional interval of said second period of time; and (j) tenth means for calculating a difference between said target chamber pressure and said optimal pressure differential, if said target chamber pressure has been reached by the conclusion of said one interval of said second period of time, to predetermine a further target chamber pressure to be reached at the conclusion of an additional interval of said second period of time.

7. The system of claim 6 wherein said second means for exhausting vapor includes a first exhaust valve.

8. The system of claim 7 wherein said sixth means for exhausting vapor includes said first exhaust valve and a second exhaust valve, said second exhaust valve being larger than said first exhaust valve.

9. The system of claim 6 wherein said first means for measuring chamber pressure, said third means for measuring chamber pressure and said seventh means for measuring chamber pressure include a pressure transducer and a microprocessor.

10. The system of claim 6 wherein said fourth means for calculating, said fifth means for calculating, said ninth means for calculating and said tenth means for calculating include a microprocessor.

* * * * *